(12) United States Patent
Bristow

(10) Patent No.: US 10,011,552 B2
(45) Date of Patent: Jul. 3, 2018

(54) PROCESS FOR PREPARATION OF HERBICIDAL CARBOXYLIC ACID SALTS

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 15/032,298

(22) PCT Filed: Jun. 19, 2014

(86) PCT No.: PCT/CN2014/080265
§ 371 (c)(1),
(2) Date: Apr. 26, 2016

(87) PCT Pub. No.: WO2015/062286
PCT Pub. Date: May 7, 2015

(65) Prior Publication Data
US 2016/0251295 A1   Sep. 1, 2016

(30) Foreign Application Priority Data
Oct. 30, 2013  (GB) .................................. 1319166.3

(51) Int. Cl.
| | | |
|---|---|---|
| C07D 213/08 | (2006.01) |
| C07D 213/79 | (2006.01) |
| C07D 213/803 | (2006.01) |
| C07D 215/08 | (2006.01) |
| C07D 215/18 | (2006.01) |
| A01N 33/08 | (2006.01) |
| A01N 37/00 | (2006.01) |
| A01N 37/40 | (2006.01) |
| A01N 39/04 | (2006.01) |
| A01N 43/40 | (2006.01) |
| A01N 43/42 | (2006.01) |
| C07C 51/41 | (2006.01) |
| C07C 51/42 | (2006.01) |
| A01N 25/12 | (2006.01) |
| A01N 37/10 | (2006.01) |
| C07C 51/47 | (2006.01) |
| C07C 59/68 | (2006.01) |
| C07C 65/21 | (2006.01) |
| C07C 213/08 | (2006.01) |
| C07C 215/08 | (2006.01) |

(52) U.S. Cl.
CPC ............ *C07C 51/412* (2013.01); *A01N 25/12* (2013.01); *A01N 33/08* (2013.01); *A01N 37/10* (2013.01); *A01N 37/40* (2013.01); *A01N 39/04* (2013.01); *A01N 43/40* (2013.01); *A01N 43/42* (2013.01); *C07C 51/42* (2013.01); *C07C 51/47* (2013.01); *C07C 59/68* (2013.01); *C07C 65/21* (2013.01); *C07C 213/08* (2013.01); *C07C 215/08* (2013.01); *C07D 213/79* (2013.01); *C07D 213/803* (2013.01); *C07D 215/18* (2013.01)

(58) Field of Classification Search
None
See application file for complete search history.

(56) References Cited

U.S. PATENT DOCUMENTS

| | | | |
|---|---|---|---|
| 3,013,054 A * | 12/1961 | Richter | ................... C07C 45/54 544/107 |
| 4,022,610 A | 5/1977 | Hokama | |
| 4,760,177 A | 7/1988 | Amiet | |
| 5,266,553 A | 11/1993 | Champion et al. | |
| 5,336,806 A | 8/1994 | Qi | |
| 5,939,584 A | 8/1999 | Merkle et al. | |
| 2003/0199709 A1 | 10/2003 | Brown et al. | |
| 2004/0133023 A1 | 7/2004 | Hasegawa | |
| 2013/0316907 A1 | 11/2013 | Kravets | |

FOREIGN PATENT DOCUMENTS

| | | |
|---|---|---|
| CN | 1340508 A | 3/2002 |
| CN | 1443153 A | 9/2003 |
| CN | 103025701 A | 4/2013 |
| FR | 2588863 A1 | 4/1987 |
| GB | 780642 A | 8/1957 |
| GB | 1301197 A | 12/1972 |
| RO | 115685 B1 | 5/2000 |

(Continued)

OTHER PUBLICATIONS

Rogers, RD. et al. Ionic liquid forms of the herbicide dicamba with increased efficacy and reduced volatility. Green Chemistry. 2013, vol. 15, p. 2111.*

(Continued)

*Primary Examiner* — Timothy R Rozof
(74) *Attorney, Agent, or Firm* — Dickinson Wright PLLC

(57) ABSTRACT

A process for preparing a herbicidally active carboxylic acid salt is disclosed. The process comprises the steps of:

i) combining a carboxylic acid with a high-boiling, water-immiscible organic solvent to obtain a solution or slurry;

ii) treating the solution or slurry produced in step (i) with a base to form a carboxylic acid salt;

iii) removing solvent from the mixture produced in step (ii) to obtain a carboxylic acid salt cake; and v) drying the cake obtained in step (iii).

The process is particularly suitable for preparing a salt of dicamba.

19 Claims, No Drawings

(56) References Cited

FOREIGN PATENT DOCUMENTS

WO         9620155 A1    7/1996
WO    2011143690 A1   11/2011

OTHER PUBLICATIONS

Goldman, IM. Activation of Manganese Dioxide by Azeotropic Removal of Water. 1969, vol. 34, p. 1979.*
Andrew Rollins et al., "Xenobiotic Monitoring in Plants" by 19F and 1H Nuclear Magnetic Resonance Imaging and Spectroscopy, Jan. 1, 1989.
French Search Report and Written Opinion dated Dec. 7, 2015.
International Search Report and Written Opinion dated Sep. 26, 2014.
Intellectual Property Office, Patent Act 1977: Combined Search and Examination Report under Sections 17 and 18(3), May 13, 2014.
Supplementary Search Report and Written Opinion dated May 15, 2017.

* cited by examiner

PROCESS FOR PREPARATION OF HERBICIDAL CARBOXYLIC ACID SALTS

This application is a 371 national phase entry of PCT/CN2014/080265, filed 19 Jun. 2014, which claims benefit of GB Patent Application No. 1319166.3, filed Oct. 30, 2013, the entire contents of which are incorporated herein by reference for all purposes.

FIELD OF THE INVENTION

The present invention relates to a process for preparation of carboxylic acid salts having herbicidal activity.

BACKGROUND

Herbicidally active carboxylic acids such as benzoic acids, phenoxy carboxylic acids, pyridine carboxylic acids and quinoline carboxylic acids have been found to be useful in controlling the growth of weeds in various crops. In particular, these carboxylic acids are classified as growth regulating herbicides and act as synthetic auxins in preventing the growth of weeds in crops. In use to control the growth of unwanted plants, a herbicidally effective amount of one or more of these carboxylic acid herbicides is applied to the locus of weeds, generally with one or more agriculturally acceptable carriers, surfactants and other additives.

It is known to apply herbicidally active carboxylic acids to susceptible vegetation in their acid forms. However, their herbicidal effectiveness is poor because the water-insoluble acid forms do not penetrate the leaves of susceptible vegetation sufficiently for fast and efficient control and eradication. Therefore, the herbicidally active carboxylic acids are traditionally converted from the acid forms into esters or salts, in order to enhance water solubility and leaf penetration properties. Both the ester and salt forms of such herbicidally active carboxylic acids are available commercially.

A conventional method of preparing carboxylic acid salts is to react an aqueous carboxylic acid solution with an alkali metal- or ammonium-containing alkaline solution to produce the corresponding carboxylic acid salt and water. The carboxylic acid salt is typically then dried to form a solid herbicide.

U.S. Pat. No. 3,013,054 discloses the preparation of sodium 2-methoxy-3,6-dichlorobenzoate. In the process disclosed, 2-methyoxy-3,6-dichlorobenzoic acid (116 g; 0.5 mol) is dissolved in 500 cc of methanol and treated with a solution of sodium hydroxide (20 g; 0.5 mol) in 100 cc of methanol. Methanol is removed by distillation in vacuo over a steam bath and the solid residue is slurried with 100 cc of cold dry ether, filtered, pressed dry, and dried completely in a vacuum oven to give the desired salt, sodium 2-methoxy-3,6-dichlorobenzoate.

U.S. Pat. No. 5,266,553 suggests to prepare solid salts by neutralization of the corresponding aryloxycarboxylic acids with a base, followed by conversion of the resulting aqueous solution into the solid salts by evaporating water under controlled conditions. The solid salts can also be prepared by evaporating water from the corresponding commercially available aryloxy salt solutions.

One issue arising with these known methods is cost. In particular, to dry the carboxylic acid salt after its formation, the salt solution must be heated. As a result of the large volume of water used in the preparation of the acid solution and produced during formation of the carboxylic acid salt, it is expensive to provide the necessary amount of heat energy to dry the carboxylic acid salt solution.

Another issue related to the production of carboxylic acid salts is the pH of the carboxylic acid salt solutions. Various methods have been employed to control the pH of the carboxylic acid salt solutions and the resulting carboxylic acid salts. In particular, as the resulting carboxylic acid salts are generally re-dissolved in water for their eventual use, it is important to have salts that have a suitable pH when dissolved in water. One method of controlling the pH of the carboxylic acid salts is to neutralize the solution as needed prior to drying. For example, buffers, such as alkaline compounds, have been combined with the carboxylic acid salts to produce the desired pH for the carboxylic acid solution.

U.S. Pat. No. 5,266,553 describes a method of producing carboxylic acid salts by forming the carboxylic acid salts from the carboxylic acid and an alkaline compound, followed by reacting the carboxylic acid salt with a second alkaline buffer compound to produce a carboxylic acid salt having increased water solubility. An alternative method of controlling the pH of the salts is to prepare different batches of carboxylic acid salts and mix the batches to provide the desired pH value. However, it is difficult to dry salts, particularly when they are sticky, and produce a consistent product.

Another issue with the known methods is production yield and purity. The prior art provides processes, which are applicable for use on a laboratory scale.

However, for production on an industrial scale, the problems of low yield and purity remain unsolved.

Accordingly, there is a need for an improved process for preparing solid, free-flowing and readily water-soluble carboxylic acid salts, in particular applicable for use on an industrial scale.

SUMMARY

According to an embodiment of the present invention, there is provided a process for preparing a herbicidally active carboxylic acid salt, the process comprising the steps of:
i) combining a carboxylic acid in a high-boiling, water-immiscible organic solvent to obtain a solution or slurry;
ii) treating the solution or slurry produced in step (i) with a base to form a carboxylic acid salt;
iii) removing solvent from the mixture produced in step (ii) to obtain a carboxylic acid salt cake; and
iv) drying the cake obtained in step (iii).

The process is suitable for preparing solid, free-flowing and readily water-soluble herbicidally active carboxylic acid salts, in particular suitable for use on an industrial scale. The process allows the herbicidal carboxylic acid salts to be produced at a lower cost than known processes, in particular due to the lower energy requirement. The process also has improved environmental-friendliness.

DETAILED DESCRIPTION

The process according to an embodiment of the present invention is applied to a herbicidally active carboxylic acid. The process may be applied to any herbicidally active compound with a carboxylic acid functionality. Such herbicidally active carboxylic acids are known in the art, with many being commercially available. Preferably the carboxylic acids are selected from benzoic acids, phenoxy carboxylic acids, pyridine carboxylic acids and quinoline carboxylic acids.

Preferred benzoic acid herbicides are 2-methoxy-3,6-dichlorobenzoic acid (dicamba); 3,5-6-trichloro-o-anisic acid (tricamba); 3-amino-2,5-dichlorobenzoic acid (chloramben); 5-2[2-chloro-4-(trifluoromethyl)phenoxy]-2-nitrobenzoic acid; 2,3,5-triiodobenzoic acid; and trichlorobenzoic acid. Preferred phenoxy carboxylic acid herbicides are 2,4-dichlorophenoxyacetic acid (2,4-D); 4-(2,4-dichlorophenoxy)butyric acid (2,4-DB); 2-(2,4-dichlorophenoxy)propionic acid (2,4-DP); 2,4,5-trichlorophenoxyacetic acid (2,4,5-T); 2-(2,4,5-trichlorophenoxy)propionic acid; 4-chloro-2-methylphenoxyacetic acid (MCPA); 2-(4-chloro-2-methylphenoxy)propionic acid (MCPP); 4-(4-chloro-2-methylphenoxy)butyric acid (MCPB); and 2-[4-(2',4'-dichlorophenoxy)-phenoxy]propanoic acid. Preferred pyridine carboxylic acid herbicides are 4-amino-3,5,6-trichloropicolinic acid (picloram); 3,5,6-trichloro-2-pyridyloxyacetic acid (triclopyr); clopyralid; and fluroxypyr. Preferred quinoline carboxylic acid herbicides are selected from quinclorac and quinmerac.

The process is particularly suitable for applying to benzoic acid herbicides, especially dicamba.

The process according to an embodiment of the present invention employs a solvent. The solvent is a high-boiling, water-immiscible organic solvent. The solvent is substantially inert, that is does not react with the carboxylic acid or the salt thereof. To achieve good separability from the reaction mixture and carboxylic acid salt in a customary manner with higher production yield, a suitable solvent should preferably exhibit low/no solvation power to the carboxylic acid salt produced in the process.

The solvent is combined with the carboxylic acid to form a solution or a slurry. Suitable solvents include any solvent which functions as a solvent and/or an entrainer for the carboxylic acid starting material.

The solvent has a high boiling point. In general, a high boiling point solvent is one having a boiling point above 70° C. The boiling point of the solvent is preferably above 80° C.

Suitable organic solvents, include aromatic solvents, such as toluene and xylene, and the higher, water-immiscible alcohols, such as n-butanol and iso-butanol, pentanols, hexanols, heptanols and mixtures thereof.

In one embodiment of the process, the aforementioned high-boiling, water-immiscible, inert organic solvent is suitable for dissolving the carboxylic acid and is advantageously employed in at least an amount such that the carboxylic acid is dissolved or well suspended. Preferably, the carboxylic acid starting material is soluble in the selected organic solvent and sufficient solvent is used to form a solution of the carboxylic acid.

In a preferred embodiment, the above mentioned high-boiling water-immiscible inert organic solvent functions as an entrainer and is suitable for removal of water from the reaction mixture. Water may be present in the base, for example when the base is employed in the form of an aqueous solution, and/or may be generated from the reaction between the carboxylic acid and the base. In particular, it is preferred that the organic solvent forms an azeotrope with water. In this way, water may be removed from the reaction mixture by azeotropic distillation.

In this embodiment, water present in the base and/or generated during formation of the carboxylic acid salt is removed together with the high-boiling, water-immiscible, inert organic solvent by azeotropic distillation. In particular, azeotropic distillation may be performed on the reaction mixture to remove the solvent and water while the reaction between the carboxylic acid and the base is taking place. The boiling point of the azeotrope is determined by the selected solvent. For example, xylene forms an azeotrope with water comprising 60% xylene and having a boiling point of 94.5° C. Toluene forms an azeotrope with water comprising 80% toluene and having a boiling point of 85° C.

In one embodiment, the solvent is selected such that the boiling point of the solvent/water azeotrope is higher than the reaction temperature. In this way, water and the solvent may be removed from the reaction mixture after the reaction has taken place.

If the reaction temperature is above the boiling point of the azeotrope, the solvent/water mixture may be removed from the reaction mixture by evaporation. In particular, heat released as a result of the reaction between the carboxylic acid and the base may be used to evaporate the solvent/water azeotrope. In this way, water generated from the reaction between the carboxylic acid and the base can be simultaneously removed from the reaction mixture by evaporation of the azeotrope, for example by subjecting the reaction mixture to azeotropic distillation while the reaction is taking place. In a preferred embodiment, the solvent is selected such that the boiling point of the solvent/water azeotrope is close to, that is within +/−5° C., more preferably +/−3° C., or substantially the same as the reaction temperature. In other words, in a preferred embodiment, the reaction is conducted at a temperature close to or at the boiling point of the solvent/water azeotrope The organic solvent is preferably selected to have a relatively high solvation power with respect to the carboxylic acid and a lower solvation power with respect to the salt, that is that the carboxylic acid is readily soluble in the solvent, while the salt is sparingly soluble or substantially insoluble in the solvent. The solvent may also be selected to have a high solvation power for impurities, such as chlorophenols, phenoxy acid and other organic impurities, which may be present in the carboxylic acid starting material, that is the impurities are readily soluble in the solvent. In this way, any carboxylic acid remaining after reaction with the base and any impurities can be conveniently removed from the salt product.

Conversion of the carboxylic acid into its salt can be carried out using any suitable base. The base may be organic or inorganic. Preferred bases are bases of Group I or Group II metals, such as potassium, sodium, calcium and magnesium. Group I metal bases are particularly preferred, especially bases of sodium or potassium. Bases comprising ammonium ions are also particularly suitable for use in the process according to embodiments of this invention. Suitable organic bases include amines.

Examples of suitable bases include without limitation: alkali metal hydroxides, for example sodium hydroxide and potassium hydroxide; alkali metal oxides; alkali metal carbonates and hydrogen carbonates, for example potassium carbonate, sodium carbonate, potassium bicarbonate, sodium bicarbonate; alkali metal acetates and formates, for example sodium acetate; ammonia; and alkyl-substituted primary, secondary and tertiary amines having 1 to 4 carbon atoms, for example ethanolamine, and 1,2-ethanediamine.

As noted above, appropriate selection of the organic solvent allows for water to be easily removed from the reaction mixture or the reaction product, together with the solvent. Accordingly, the base may be employed in the form of an aqueous solution.

The reaction between the carboxylic acid and the base can be carried out under any suitable conditions of temperature and pressure. Suitable temperatures range from 50° C. to 250° C., preferably from 50° C. to 200° C., more preferably from 60° C. to 200° C., even more preferably from 60° C. to 150° C., still more preferably from 80° C. to 150° C. A temperature in the range of from 90° C. to 150° C. is particularly suitable in many embodiments. The reaction may be conducted most conveniently at normal or atmospheric pressures.

The formed carboxylic acid salts and the organic solvent may be separated by any suitable technique. The salt and the solvent are preferably separated by centrifugation, on account of the insolubility of the carboxylic acid salts in the solvent. The salts can be further dried by conventional drying processes, for example, contact or convective drying processes conducted at a suitable temperature, such as 50° C. to 80° C. under a reduced pressure.

Acid forms of herbicidal compounds are generally water-insoluble. Accordingly, if a sufficient amount of the acid form of the herbicidal compound is present in the salt, the herbicidal salt composition is not completely soluble in water. Therefore, conventional methods of isolating salts include the use of an excess amount of a base in the herbicidal composition. This excess amount of neutralizing base causes the composition to have a high pH, leading to possible problems of corrosion. When employing an amine as the neutralizing base, the composition can also have a nauseating "fishy" odor.

Surprisingly, it has been found that, in the process, the carboxylic acid does not have to be completely neutralized by the base to provide an essentially completely water-soluble, herbicidally active carboxylic salt composition. The water-soluble herbicidal carboxylic salt can be isolated as long as at least 97% of the carboxylic acid is neutralized. In other words, it is only necessary to provide at least 97% of the stoichiometric amount of base required to react with the carboxylic acid in step (ii). Accordingly, excess amounts of the base are not required. As a result, the product of the process is less corrosive and less odorant, such as when using ammonia or an ammonia derivative as the base. In the process, the base is preferably used in an amount from about 97 to about 100 mole percent, within about 1%, preferably 0.6% variation, of the amount sufficient to neutralize the carboxylic acid starting material. The amount and the precision of feeding rate of the base sufficient to neutralize the carboxylic acid within the desired pH limits can be determined by titration methods known in the art.

As noted above, the process is particular suitable for use with dicamba. Accordingly, in one preferred embodiment, dicamba-sodium is prepared by mixing dicamba and a base at a molar ratio of 1:0.97±0.6%, that is from 1:0.964 to 1:0.976. The base is preferably an alkali metal base, in particular a sodium base, for example selected from sodium hydroxide, sodium bicarbonate and mixtures thereof. It has been found that controlling the ratio of dicamba and the base within the aforementioned range provides the benefit of producing dicamba-sodium consistently having a pH between about 7 and 10 when dissolved in water.

The carboxylic acid salt and any remaining carboxylic acid dissolved or suspended in the high-boiling, water-immiscible organic solvent are separated in step (iii), for example by a centrifuge, where the carboxylic acid salt is separated from the organic solution to obtain a carboxylic acid salt cake. The cake of carboxylic acid salt is then advanced to a dryer where any remaining water and solvent are removed. Dry carboxylic acid salt is recovered as a product and does not require buffers or batch mixing to adjust its pH value.

The carboxylic acid salts prepared by the process are produced at a lower cost owing to reduced heating costs during their formation. Water used in preparation of the base and/or generated during formation of the carboxylic acid salt may be removed with the high-boiling water-immiscible inert organic solvent, in particular by azeotropic distillation, and then isolated with the solvent. The heat released during the reaction can be utilized directly to evaporate the azeotrope. The carboxylic acid salt may be recovered as a cake from any remaining carboxylic acid through centrifugation. The cake of carboxylic acid salt may be fed to a dryer, where any remaining water and solvent are removed. As a result, the costs for heating in the whole preparation of carboxylic acid salt are reduced, compared with known processes. In addition, water produced in the reaction may be removed by azeotropic distillation. This in turn brings economic benefits as less energy is required to dry the carboxylic acid salt.

Furthermore, the process can produce carboxylic acid salts at higher yields and purity, in particular because the high-boiling, water-immiscible, inert organic solvent can be selected to have a high solvation power for the carboxylic acid and impurities, but a lower solvation power for the carboxylic acid salt.

The following examples illustrate example embodiments of the invention. It should be understood, however, that the invention is not limited solely to the particular examples given below.

EXAMPLES

Example 1 Preparation of Dicamba-Sodium

Dicamba (116 g; 0.5 mol) was dissolved in 1160 g of toluene in a mixer. A solution of sodium hydroxide (19.3 g, 0.48 mol) in 38.6 mL water was added, and the reaction mixture was refluxed for 2 hours, maintaining the reaction temperature at the boiling point of the toluene/water azeotrope. Toluene and water were evaporated during the reaction, condensed, and collected by a manifold. The formed dicamba salt was then separated from the cooled reaction mixture by centrifugation to form a cake. The cake was dried in a vacuum oven to give dicamba-sodium, with a pH value of 7 in water. The yield of dicamba-sodium salt was 95%.

Example 2 Preparation of MCPA-Potassium

MCPA (20 g; 0.1 mol) was dissolved in 200 g of xylene in a mixer. 100 mL of potassium hydroxide solution (0.1 M) was added at 90° C. to 95° C., and the reaction mixture was refluxed for 2 hours, maintaining the reaction temperature at the boiling point of the toluene/water azeotrope. Xylene and water were evaporated during the reaction, condensed, and collected by a manifold. The formed MCPA salt was then separated from the cooled reaction mixture by centrifugation to form a cake. The cake was dried in a vacuum oven to give the desired salt, MCPA-potassium, with a pH value of 9 in water. The yield of MCPA-potassium was 98%.

Example 3 Preparation of Clopyralid-bis(2-hydroxyethyl)ammonium

Clopyralid (192 g; 1 mol) was dissolved in 2000 g of n-butanol in a mixer. 61 mL of ethanolamine (1 mol) was added at 85° C. to 90° C., and the reaction mixture was refluxed for 2 hours, maintaining the reaction temperature at the boiling point of the toluene/water azeotrope. n-Butanol and water were evaporated during the reaction, condensed, and collected by a manifold. The formed clopyralid salt was then separated from the cooled reaction mixture by centrifugation to form a cake. The cake was dried in a vacuum oven to give the desired salt, clopyralid-bis(2-hydroxyethyl)ammonium, having a pH value of 8 in water. The yield of clopyralid-bis(2-hydroxyethyl)ammonium was 96%.

Example 4 Preparation of Quinclorac-Sodium

Quinclorac (242 g; 1 mol) was dissolved in 2000 g of n-hexanol in a mixer. 168 mL of sodium bicarbonate (1 M) was added at 90° C. to 95° C. The reaction mixture was refluxed for 2 hours, maintaining the reaction temperature at the boiling point of the toluene/water azeotrope. n-Hexanol and water were evaporated during the reaction, condensed, and collected by a manifold. The formed quinclorac salt was then separated from the cooled reaction mixture by centrifugation to form a cake. The cake was then dried in a vacuum oven to give the desired salt, quinclorac-sodium, which had a pH value of 10 in water. The yield of quinclorac-sodium was 98%.

The invention claimed is:

1. A process for preparing a herbicidally active carboxylic acid salt, wherein the herbicidally active carboxylic acid salt is salt of a carboxylic acid selected from the group consisting of dicamba, tricamba, 2,4-D, MCPA, picloram, clopyralid, and quinclorac the process comprising the steps of:
   i) combining a carboxylic acid wherein the carboxylic acid is selected from the group consisting of dicamba, tricamba, 2,4-D, MCPA, picloram, clopyralid, and quinclorac, with a water-immiscible organic solvent that forms an azeotrope with water, to obtain a solution or slurry;
   ii) treating the solution or slurry produced in step (i) with a base to form a carboxylic acid salt at a temperature that is within +/−5° C. of the boiling point of the azeotrope;
   iii) removing solvent from the mixture produced in step (ii) to obtain a carboxylic acid salt cake; and
   iv) drying the cake obtained in step (iii).

2. The process according to claim 1, wherein the carboxylic acid is dicamba.

3. The process according to claim 1, wherein the solvent exhibits a lower solvation power for the carboxylic acid salt than for the carboxylic acid and impurities.

4. The process according to claim 1, wherein the carboxylic acid is soluble in the solvent.

5. The process according to claim 1, wherein the solvent has a boiling point of at least 70° C.

6. The process according to claim 1, wherein the solvent is selected from toluene, xylene, n-butanol, pentanols, hexanols, heptanols and mixture thereof.

7. The process according to claim 6, wherein in step (iii) the solvent is removed together with water while the reaction between the carboxylic acid and the base in step (ii) is taking place.

8. The process according to claim 7, wherein the solvent and water are removed by azeotropic distillation.

9. The process according to claim 6, wherein the boiling point of the azeotrope is below the reaction temperature of step (ii).

10. The process according to claim 1, wherein the base is an inorganic base.

11. The process according to claim 10, wherein the base is of a Group I or Group II metal or an ammonium compound.

12. The process according to claim 11, wherein the base is selected from alkali metal hydroxides, alkali metal oxides, alkali metal carbonates, alkali metal hydrogen carbonates, alkali metal acetates, alkali metal formats and ammonia.

13. The process according to claim 1, wherein the base is an organic base.

14. The process according to claim 13, wherein the base is an alkyl-substituted primary, secondary and tertiary amines having 1 to 4 carbon atoms.

15. The process according to claim 1, wherein the base is provided in step (ii) as an aqueous mixture or solution.

16. The process according to claim 1, wherein the reaction in step (ii) is conducted at a temperature of from 50° C. to 200° C.

17. The process according to claim 1, wherein from 97% to 100% of the stoichiometric amount of base required to react with the carboxylic acid is provided in step (ii).

18. The process according to claim 1, wherein the solvent is removed in step (iii) by centrifugation.

19. A process of making dicamba-sodium, comprising the steps of:
   (1) dissolving a carboxylic acid consisting essentially of dicamba in a high-boiling water-immiscible inert organic solvent to get a solution or slurry;
   (2) treating the dicamba solution or slurry in Step 1 with a base selected from sodium hydroxide, sodium bicarbonate and mixtures thereof, at a molar ratio of 1:0.97±0.6% to form dicamba-sodium;
   (3) centrifuging the reaction mixture in Step 2 to obtain dicamba-sodium salt cake; and
   (4) drying the dicamba-sodium cake obtained in Step 3 to get a dry dicamba-sodium consistently having a pH value between about 7 and 10 when dissolved in water.

* * * * *